United States Patent [19]
Hollenberg et al.

[11] Patent Number: 5,389,525
[45] Date of Patent: Feb. 14, 1995

[54] DNA-MOLECULES CODING FOR FMDH CONTROL REGIONS AND STRUCTURAL GENE FOR A PROTEIN HAVING FMDH-ACTIVITY AND THEIR USE THEREOF

[75] Inventors: Cornelius P. Hollenberg, Dusseldorf; Zbigniew Janowicz, Erkrath, both of Germany

[73] Assignee: Rhein Biotech, Dusseldorf, Germany

[21] Appl. No.: 844,885

[22] Filed: Mar. 3, 1992

Related U.S. Application Data

[63] Continuation of Ser. No. 248,519, Sep. 23, 1988, abandoned.

[51] Int. Cl.$^6$ .................. C12P 21/02; C12N 15/81; C12N 15/52; C12N 1/19
[52] U.S. Cl. .................. 435/69.1; 435/254.2; 435/320.1; 536/23.2; 536/24.1
[58] Field of Search .............. 435/172.3, 172.1, 191, 435/320.1, 255, 69.1, 930, 938; 536/27, 24.1, 23.2; 935/28, 37, 69, 254.2

[56] References Cited

U.S. PATENT DOCUMENTS

| | | | |
|---|---|---|---|
| 4,855,231 | 8/1989 | Stroman et al. | 435/172.3 |
| 4,876,197 | 10/1989 | Burke et al. | 935/28 |
| 4,886,750 | 12/1989 | Bertola et al. | 435/830 |

FOREIGN PATENT DOCUMENTS 0183071 6/1986 European Pat. Off. ...... C12N 15/00

OTHER PUBLICATIONS

Ledeboer, A. M., et al., "Molecular cloning and characterization of a gene coding for methanol oxidase in Hansenula polymorpha," Nucleic Acids Research, vol. 13, No. 9, pp. 3063–3081 (1985).
Janowicz, Z. A., et al., "Cloning and characterization of the DAS gene encoding the major methanol assimilatory enzyme from the methylotrophic yeast Hansenula polymorpha," Nucleic Acids Research, vol. 13, No. 9, 3043–3062 (1985).
Allais, J. J., et al., "Oxidation of Methanol by the Yeast *Pichia pastoris*. Purification and Properties of the Formate Dehydrogenase," Agric. Biol. Chem., 47 (11), pp. 2547–2554 (1983).
Cregg, J. M., et al., "High-Level Expression and Efficient Assembly of Hepatitis B Surface Antigen in the Methylotrophic Yeast, *Pichia Pastoris*," Bio Technology, vol. 5, pp. 479–485 (May 1987).
Hinnen, A., "Yeast As an Expression System for Heterologous Proteins," Elsevier Science Publishers B. V., Amsterdam (1987).
Tschopp, J. F., et al., "Expression of the lacZ gene from two methanol-regulated promoters in *Pichia pastoris*," Nucleic Acids Research, vol. 15, No. 9, pp. 3859–3876 (1987).
Roa, Michele, et al., "Biosynthesis of peroxisomal enzymes in the methylotrophic yeast *Hansenula polymorpha*", Proc. Natl. Acad. Sci. U.S.A., vol. 80, pp. 6872–6876 (Nov. 1983).

(List continued on next page.)

*Primary Examiner*—Richard A. Schwartz
*Assistant Examiner*—James Ketter
*Attorney, Agent, or Firm*—Finnegan, Henderson, Farabow, Garrett & Dunner

[57] ABSTRACT

The invention relates to DNA-molecules comprising DNA-sequences encoding control regions and the structural gene for a protein having formate dehydrogenase (FMDH) activity. Said DNA-molecules may be combined with DNA-sequences encoding foreign genes so as to bring these genes under the stringent control of the regulation of the FMDH regulatory sequences and/or may be combined to DNA-sequences coding for secretory signals. The invention further relates to recombinant vectors containing said DNA-molecules and micro-organisms containing said vectors or DNA-molecules. Furthermore, the invention relates to a process for producing a useful substance by producing this substance by culturing said micro-organisms and recovering the substance.

20 Claims, 13 Drawing Sheets

OTHER PUBLICATIONS

Ellis, S. B., et al. "Isolation of Alcohol Oxidase and Two Other Methanol Regulatable Genes from the Yeast *Pichia pastoris*", Molecular and Cellular Biology, pp. 1111-1121 (May 1985).

Shuber, A. P. et al., "Cloning, Expression, and Nucleotide Sequence of the Formate Dehydrogenase Genes from *Methanobacterium fromicicum*", Journal of Biological Chemistry vol. 261, No. 28: pp. 12942-12947 (Oct. 1986).

Zioni, F., "Nucleotide sequence and expression of the selenocysteine-containing polypeptide of formate dehydrogenase (formate-hydrogen-lyase-linked) from *Escherichia coli*", Proc. Natl. Acad. Sci. U.S.A., vol. 83, pp. 4650-4654 (Jul. 1986).

An International Journal on Morphology, Physiology, Genetics, and Ecology of Microorganisms, Journal of Basic Microbiology, vol. 28, 1988.

M. A. Gleeson and P. E. Sudbery, The Methylotrophic Yeasts, Yeast, vol. 4: 1-15 (1988).

Shuber et al. (1986) "Formate dehydrogenase genes from *Methanobacterium formicium*," vol. 261, JBC, pp. 12942-12947.

Avilova et al. (1985) "Formate dehydrogenase from yeast," vol. 152, E. J. of Biochem, pp. 657-662.

Janowicz et al. (1985) "DAS gene from yeast *H. polymorpha*," vol. 13, NAR, pp. 3042-3062.

Miyanohara et al. (1983), "Expression of hepatitis B surface antigen gene in yeast," vol. 80, PNAS, pp. 1-5.

Shavlovskii et al. (1987) "Participation of Iron in the Regulation of Formate Dehydrogenase," vol. 56, Mikrobiologiya, pp. 181-185.

FIG. 5A

```
          10        20        30        40        50        60
ATCGCAGAAATGTATCTAAACGCAAACTCCGAGCTGGAAAAATGTTACCGGCGATGCGCG 70        80        90       100       110       120
GACAATTTAGAGGCGGCAATCAAGAAACACCTGCTGGGCGAGCAGTCTGGAGCACAGTCT 130       140       150       160       170       180
TCGATGGGCCCGAGATCCCACCGCGTTCCTGGGTACCGGGACGTGAGGCAGCGCGACATC 190       200       210       220       230       240
CTACAAATATACCAGGCGCCAACCGAGTCTCTCGGAAAACACAGCTTCTGGATATCTTCC 250       260       270       280       290       300
GCGGCGGCGCAACGAGCCAAGAATAGTCCCTGGAGGTGACGGAATATATATGTGTGGAGG 310       320       330       340       350       360
GTAAATCTGACAGGGTGTAGCAAAGGTAATATTTTCCTAAAACATGCAATCGGCTGCCCC 370       380       390       400       410       420
GCAACGGGAAAAAGAATGACTTTGGCACTCTTCACCAGAGTGGGGTGTCCCGCTCGTGTG 430       440       450       460       470       480
TGCAAATAGGCTCCCACTGGTCACCCCGGATTTTGCAGAAAAACAGCAAGTTCCGGGGTG 490       500       510       520       530       540
TCTCACTGGTGTCCGCCAATAAGAGGACCGGCAGGCACGGAGTCTACATCAAGCTGTCTC 550       560       570       580       590       600
CGATACACTCGACTACCATCCGGGTCTCTCAGAGAGGGGAATGGCACTATAAATACCGCC 610       620       630       640       650       660
TCCTTGCGCTCTCTGCCTTCATCAATCAAATCATGAAGGTTGTACTAGTTCTCTACGACG
                                       MetLysValValLeuValLeuTyrAspA 670       680       690       700       710       720
CAGGAAAACACGCCCAAGACGAGGAAAGACTCTACGGTTGCACTGAAAACGCCCTTGGTA
laGlyLysHisAlaGlnAspGluGluArgLeuTyrGlyCysThrGluAsnAlaLeuGlyI 730       740       750       760       770       780
TCAGGGACTGGCTCGAGAAGCAGGGCCACGACGTCGTTGTCACCAGTGACAAGGAGGGGC
leArgAspTrpLeuGluLysGlnGlyHisAspValValValThrSerAspLysGluGlyG 790       800       810       820       830       840
AGAACTCTGTGCTCGAGAAGAACATCTCGGACGCAGATGTCATCATCTCCACTCCTTTCC
lnAsnSerValLeuGluLysAsnIleSerAspAlaAspValIleIleSerThrProPheH 850       860       870       880       890       900
ACCCAGCATACATCACCAAGGAGAGAATCGACAAGGCCAAGAAGCTCAAGCTACTGGTGG
isProAlaTyrIleThrLysGluArgIleAspLysAlaLysLysLeuLysLeuLeuValV
```

FIG.5B

```
     910       920       930       940       950       960
TTGCCGGAGTGGGATCCGACCACATCGACCTTGACTACATCAACCAGTCCGGCAGAGACA
 aAlaGlyValGlySerAspHisIleAspLeuAspTyrIleAsnGlnSerGlyArgAspI 970       980       990      1000      1010      1020
TTTCTGTGCTGGAGGTGACCGGTTCGAACGTCGTTTCGGTTGCCGAGCACGTTGTGATGA
 leSerValLeuGluValThrGlySerAsnValValSerValAlaGluHisValValMetT 1030      1040      1050      1060      1070      1080
CGATGCTGGTGCTGGTGAGGAACTTTGTTCCTGCTCACGAGCAGATCATCTCTGGCGGCT
 hrMetLeuValLeuValArgAsnPheValProAlaHisGluGlnIleIleSerGlyGlyT 1090      1100      1110      1120      1130      1140
GGAACGTGGCCGAGATCGCCAAGGACTCCTTCGACATCGAGGGCAAGGTCATTGCCACCA
 rpAsnValAlaGluIleAlaLysAspSerPheAspIleGluGlyLysValIleAlaThrI 1150      1160      1170      1180      1190      1200
TCGGAGCAGGCAGAATCGGCTACCGTGTGCTGGAGAGACTTGTGGCCTTCAACCCTAAGG
 leGlyAlaGlyArgIleGlyTyrArgValLeuGluArgLeuValAlaPheAsnProLysG 1210      1220      1230      1240      1250      1260
AGCTGCTCTACTACGACTACCAGTCGCTGTCGAAAGAGGCGGAGGAGAAAGTCGGCGCCC
 luLeuLeuTyrTyrAspTyrGlnSerLeuSerLysGluAlaGluGluLysValGlyAlaA 1270      1280      1290      1300      1310      1320
GCAGAGTCCACGACATCAAGGAGCTGGTTGCCCAGGCCGACATTGTCACGATCAACTGTC
 rgArgValHisAspIleLysGluLeuValAlaGlnAlaAspIleValThrIleAsnCysP 1330      1340      1350      1360      1370      1380
CACTGCACGCCGGCTCGAAGGGCCTGGTGAACGCAGAGCTGCTCAAGCACTTCAAGAAGG
 roLeuHisAlaGlySerLysGlyLeuValAsnAlaGluLeuLeuLysHisPheLysLysG 1390      1400      1410      1420      1430      1440
GCGCCTGGCTCGTCAACACCGCCAGAGGTGCCATCTGCGTGGCCGAGGACGTTGCAGCCG
 lyAlaTrpLeuValAsnThrAlaArgGlyAlaIleCysValAlaGluAspValAlaAlaA 1450      1460      1470      1480      1490      1500
CCGTCAAGAGCGGACAGCTTAGAGGATACGGTGGAGACGTGTGGTTCCCACAGCCAGCTC
 laValLysSerGlyGlnLeuArgGlyTyrGlyGlyAspValTrpPheProGlnProAlaP 1510      1520      1530      1540      1550      1560
CAAAGGACCACCCATGGAGATCCATGGCCAACAAGTACGGTGCTGGCAATGCCATGACTC
 roLysAspHisProTrpArgSerMetAlaAsnLysTyrGlyAlaGlyAsnAlaMetThrP 1570      1580      1590      1600      1610      1620
CGCACTACTCGGGCTCTGTCATTGACGCCCAGGTCAGATACGCGCAGGGCACCAAGAACA
 roHisTyrSerGlySerValIleAspAlaGlnValArgTyrAlaGlnGlyThrLysAsnI 1630      1640      1650      1660      1670      1680
TCCTGGAGTCGTTCTTCACTCAGAAGTTCGACTACAGGCCCCAGGACATCATTCTGCTGA
 leLeuGluSerPhePheThrGlnLysPheAspTyrArgProGlnAspIleIleLeuLeuA 1690      1700      1710      1720      1730      1740
ACGGCAAGTACAAGACCAAGTCGTACGGTGCCGACAAATGAGCGGTCTTGGAGGAGCTGA
 snGlyLysTyrLysThrLysSerTyrGlyAlaAspLysEnd 1750      1760      1770      1780      1790      1800
TTGGATCTAGATGAAATAGGAAATATAATTATGGCTCTACTGCGCTGCGTAAACGTCACT
```

FIG.5C fmdh1

```
        1810      1820      1830      1840      1850      1860
GTAGGCGATTTCGCTTAGCCCAAGTCCGCGATGCGGTCCGACGACACCAGAGCGCGTCCA 1870      1880      1890      1900      1910      1920
CCTCCTGTGCGCCGCACCGCCCCCAAAGGAGGTTGCGGCTGTGCGGCTCGACGCGACCAA 1930      1940      1950      1960      1970      1980
AAAAATAAGCGTCAAAAGGAGGTGTCAGGGAAGCACGCCGTGGGGCTCGAGATATATAAA 1990      2000      2010      2020      2030      2040
GCGCAGCGTAGCTTTGTCTGTCTTGCTAATGAGCGACGACCAAGCCTTGGAAATTTTCCT 2050      2060      2070      2080      2090      2100
GAAATCCCCCGTCACCCAGGACATGATCCACCACTTGGTGACGGTCACCTTACAGGTTCT 2110      2120      2130      2140      2150      2160
GCCTTGCGAGTCCTCCAAGACCATCACCCAGAAAGTCAAGTCTTCAGCCGACACAGAGCC 2170      2180      2190      2200      2210      2220
CGTGCTCAAGACCAAGCCGCTGCCCTCGCTGCATGACTTTCACCAAGCTCGTCCGCTATA 2230      2240      2250      2260      2270
CCAACGTCTACACGGGAACGTTGATGTCGACCATCGTGTTCCTCAACAGACTXCAA
```

F

Linker:

5'-NcoI-BamHI/EcoRI(blunt ended)-3'   (in B version)

Growth on YNB-medium with 1% methanol

• — Cell density
○ — Intracellular α-amylase activity
● — α-amylase activity in medium (secretion)

DNA-MOLECULES CODING FOR FMDH CONTROL REGIONS AND STRUCTURAL GENE FOR A PROTEIN HAVING FMDH-ACTIVITY AND THEIR USE THEREOF

This application is a continuation of application Ser. No. 07/248,519, filed Sep. 23, 1988, now abandoned.

DESCRIPTION

During the last decade, several yeast strains were isolated which are able to utilize methanol as an only carbon and energy source. Until recently the studies were limited to the enzymatic level and concerned mainly two species, namely *Hansenula polymorpha* and *Candida boidinii*.

The enzymatic studies revealed that in methylotrophic yeasts methanol is oxidised via formaldehyde and formate to $CO_2$ by methanol oxidase (MOX), formaldehyde dehydrogenase (FMD) and formate dehydrogenase (FMDH), respectively. $H_2O_2$ which is generated during the first oxidation step is degraded by catalase. C1 compound is assimilated by transketalase reaction of xylulose-5-(P) and formaldehyde, the latter being derived from the dissimilatory pathway. The reaction is catalysed by dihydroxyacetone synthase (DHAS).

Growth of methylotrophic yeast on methanol is accompanied by changes in total protein composition. There are 3 major and about 5 minor proteins newly synthesized. Further, the growth on methanol is accompanied by appearance of huge peroxisomes. These organelles bear some of the key enzymes involved in methanol metabolism, namely, MOX, DHAS and catalase (1). The other two methanol enzymes FMD and FMDH, are cytoplasmic proteins. In methanol grown cells, the enzymes FMDH, MOX, and DHAS constitute up to 40% of total cell protein. The methanol utilisation pathway is highly compartmentalised and the integration of these reactions is very complex.

The methanol dissimilatory enzymes are regulated by glucose catabolite repression/derepression mechanism (2). Methanol has an additional inductive effect increasing the expression level by the factor of 2-3. In *H. polymorpha*, assimilatory DHAS enzyme follows this general regulation scheme, however, during growth on limiting amounts of glucose, derepression, an additional post transcriptional mechanism, plays a role in the regulation.

Recently, 3 genes encoding peroxisomal enzymes were cloned from *H. polymorpha* and *Pichia pastoris* and the analysis of nucleotide sequences of MOX genes from *H. polymorpha* (3) and *P. pastoris* (4) and DAS gene, which encodes DHAS from *H. polymorpha* (5) revealed that a cleavable signal sequence is not required for the transport of MOX and DHAS into the peroxisome.

The promoters of some methanol genes are very efficient and their way of regulation is favourable to the industrial application. The expression of foreign proteins can be enhanced and placed under stringent control. The large amounts of proteins (MOX, DHAS) thus produced by methylotrophic yeast are stored in the peroxisomes. The understanding of this mechanism will help to solve some problems of the stability of foreign proteins in yeast.

In the field of industrial biotechnology, there is a need for microbiological regulation systems by which large amounts of a particularly desired protein can be produced under stringent control. Although there are already promoter/terminator systems available which can be used in genetic engineering systems for controlling the amount of proteins to be produced, there is still a strong need for further regulatory systems to be available since it has turned out that, in biological systems, it is advantageous to provide more systems so that the most effective one can be chosen. The present systems are far from being efficient, especially when stringent regulation and high mitotic stability is required.

It was, therefore, an object of the present invention to provide a more effective and a very easily controllable regulatory system.

The advantage of the present invention is given by providing a DNA-molecule which comprises DNA-sequences encoding control regions and the structural gene for a protein having formate dehydrogenase (FMDH) activity.

To start more comprehensive studies on basic research and biotechnological aspects of methanol utilisation, the gene encoding the cytoplasmic methanol key enzyme FMDH was cloned. The sequence of this 1020 bp long gene and its regulatory regions have been cloned. FMDH is regulated at transcriptional level by glucose catabolite repression/derepression/methanol induction mechanism.

The DNA-molecule according to this invention is extremely useful in the biotechnology industry because of the above discussed characteristic that the expression of foreign proteins can be enhanced and placed under stringent control.

DNA-molecules having sequences which code for wild type FMDH protein may be modified by recombinant DNA technology techniques as known in the art, so as to encode a protein showing improved biotechnological features. The recombinant DNA technology technique modifications may be carried out at the sequences coding for the structural gene and also the promoter of the control region. Hence, features with a view to a very important over production of useful proteins and the stringent control are thus obtained.

A preferred embodiment of the DNA-molecule of this invention is shown in FIGS. 5a, b and c.

Examples for the use of the FMDH regulatory sequences of the present invention are combinations of said DNA sequences with foreign genes encoding hepatitis B virus S1-S2-S antigen and hepatitis B virus S antigen α-amylase from *S. castellii* and glucoamylase from *S. castellii* or invertase from *Saccharomyces cerevisiae*.

The DNA-molecules of this invention may further be combined to DNA-sequences which are coding for secretory signals, such as Hansenula polymorpha membrane translocation signals, preferably those from peroxisomal proteins, methanol oxidase and dihydroxyacetone synthase, *Schwanniomces castelli* α-amylase and glucoamylase signals, or *Saccharomyces cerevisiae* α-factor and invertase signals.

Preparation of the DNA-molecules coding for control regions and the structural gene for protein having FMDH activity may be obtained from natural DNA and/or cDNA and/or chemically synthesized DNA.

Recombinant vectors can be prepared which contain the DNA sequences according to this invention either as such, coding for the regulatory regions and/or structural genes for FMDH protein and may be combined to further DNA sequences as discussed above. Recombinant vectors for the purposes of transferring DNA sequences into an expression system are commonly used in the art and may be properly chosen. For example, the λ Charon 4A phage may carry the described DNA-molecules.

As micro-organisms which are suitable for the expression of the desired genes also may be selected from known micro-organisms in the art which are adapted for recombinant DNA technologies. Micro-organisms, however, who are able to tolerate high concentrations of foreign proteins are preferred.

Most preferred are micro-organisms of the genera Candida, Hansenula or Pichia.

The mentioned micro-organisms are able to produce the desired substances either by integration of the DNA-molecules of this invention into the chromosom of the micro-organism or by maintaining the DNA-molecules on an extra chromosomal DNA-molecule via episomal vectors.

The proteins coded by foreign genes combined to the DNA-molecules of the present invention and being produced by the transformed micro-organisms can be obtained by culturing said micro-organisms in a manner known in the art and recovering the proteins as is also standard knowledge in the art.

The invention is now presented, in a more detailed manner, by the following specification and figures. The figures show:

Lanes 7–9 Coomassie Blue stained gel; protein crude extracts from induced, derepressed and uninduced cells, respectively. Lane 10, purified FMDH. Lanes 1–3 $^{35}$S-labelled in vitro translation products of mRNA isolated from induced, uninduced cells and fractionated mRNA enriched in FMDH mRNA species, respectively. Lane 4, immunoprecipitation of translation products from lane 1. Lane 5, translation of hybrid-selected mRNA. Lane 6, immunoprecipitation of translation products from lane 5.

Figure 2:
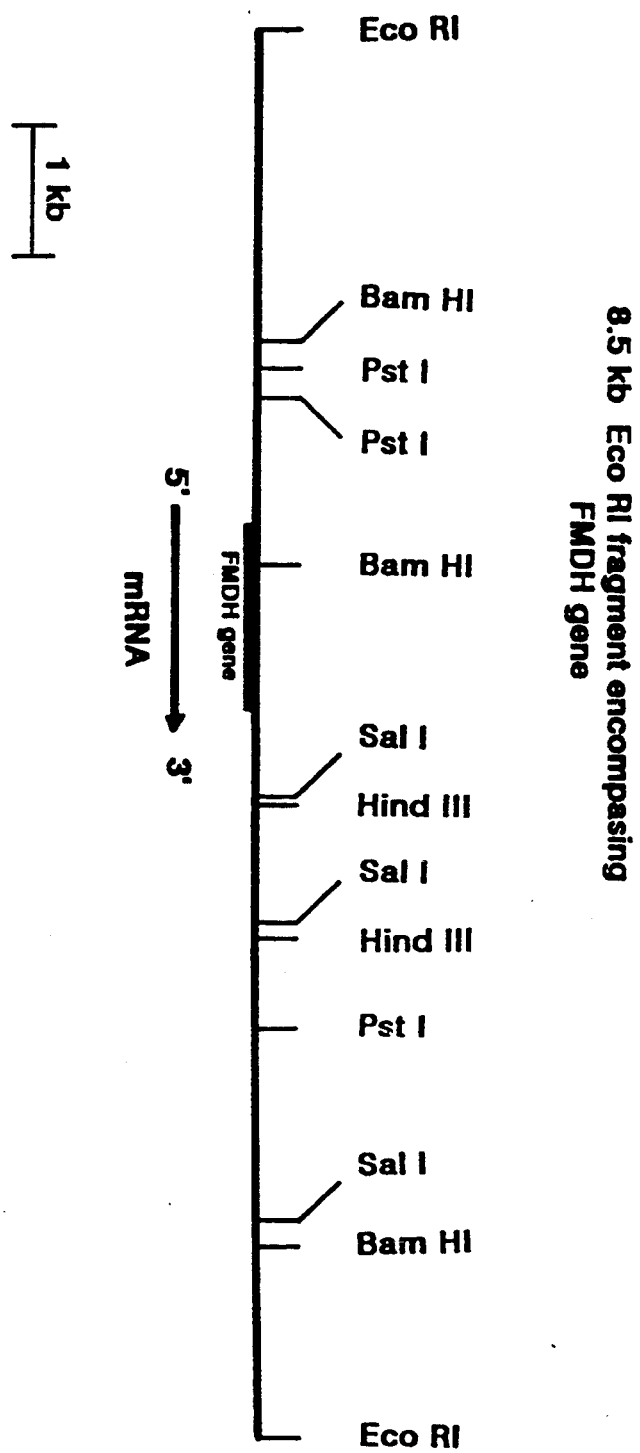

FIG. 2: Restriction map of DNA fragment encompassing the FMDH gene.

The arrow shows the direction of transcription.

Figure 3:
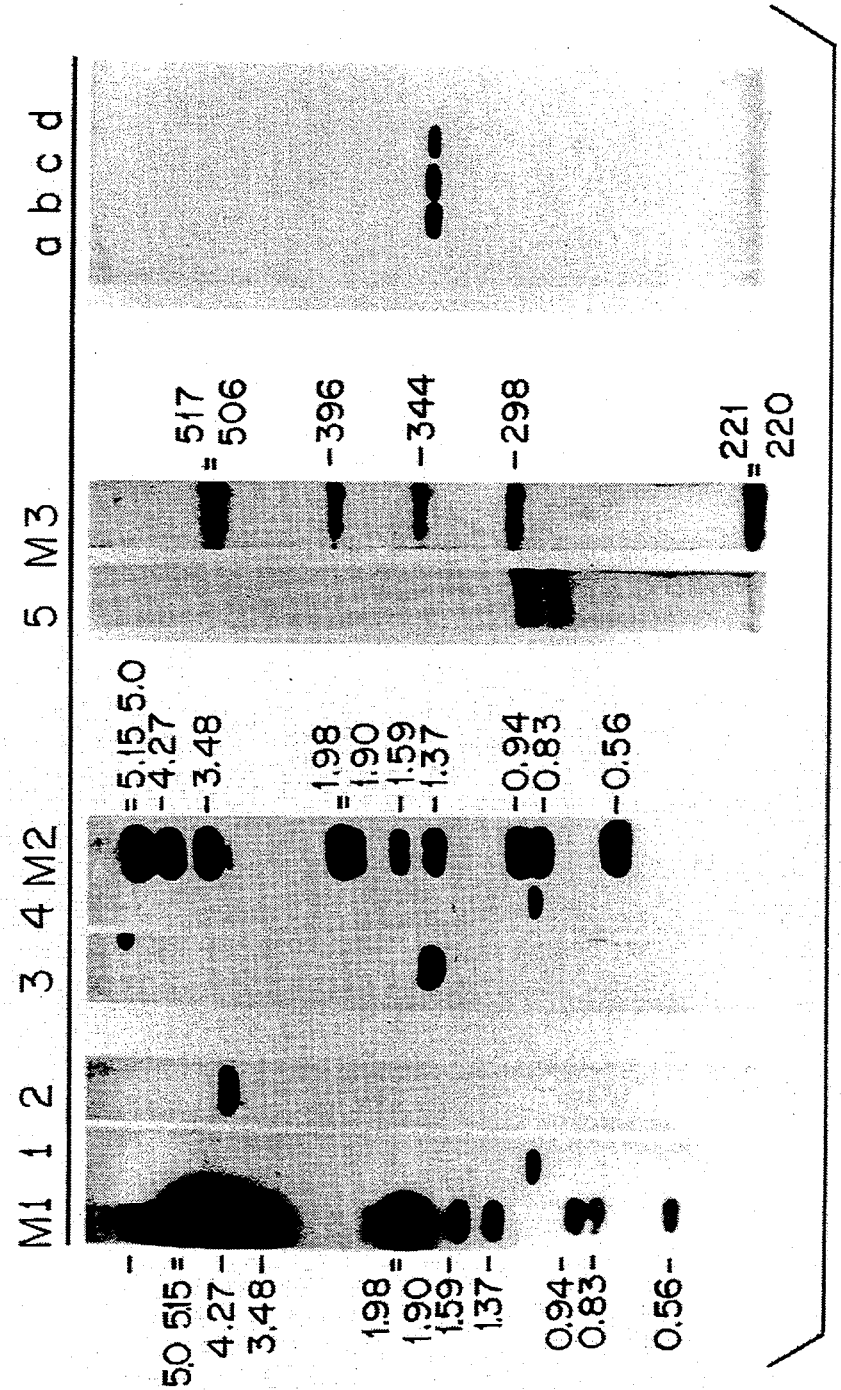

FIG. 3: S1-mapping;

Lanes M1, 1, 2, 3, 4, M2, a, b, c, d, separation on alkaline agarose gel. Lanes 5, M3-separation on 6% polyacrylamide gel/8M urea. Lanes M1-M3-MW markers. Lanes 1, 2-total protection (1) of 4.1 kb Eco-RI/Hind III fragment (2) encompassing the gene. Lanes 3, 4-protection of 3'-end labelled 1.4 kb Bam HI/Hind III fragment; 3-protected band; 4–1.4 kb intact band. Lane 5-protection of 1 kb Bam HI/Pst I fragment with a single label at Bam HI site. Lanes a, b, c, d-protection of 3'-end labelled DNA fragment containing part of the gene by mRNA preparation isolated from: induced, derepressed (1% glicerol), stationary phase of 3% glucose and mid-log phase of 3% glucose cultures, respectively.

Figure 4:
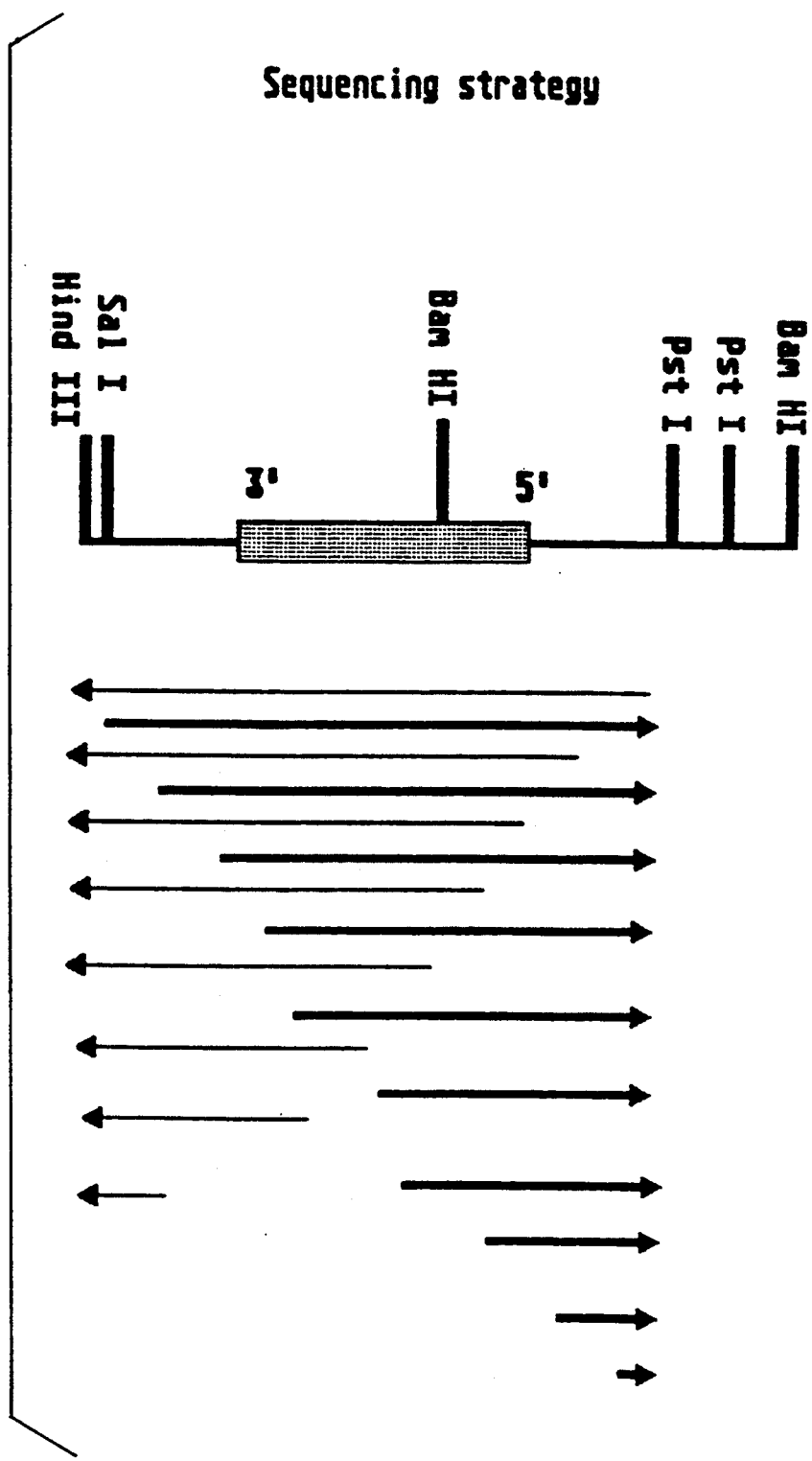

FIG. 4: Sequencing strategy—schematic representation.

DNA fragments containing the gene were subjected to Bal31 digestion and the resulting fragments subcloned into M13 and/or pUC type vectors. The fragments were sequenced by Sanger and in the case of doubts Maxam-Gilbert methods.

FIG. 5a: Nucleotide sequence of FMDH gene and its 5', 3' control regions.

FIG. 5b: Nucleotide sequence of FMDH gene and its 5', 3' control regions.

FIG. 5c: Nucleotide sequence of FMDH gene and its 5', 3' control regions.

Figure 6:
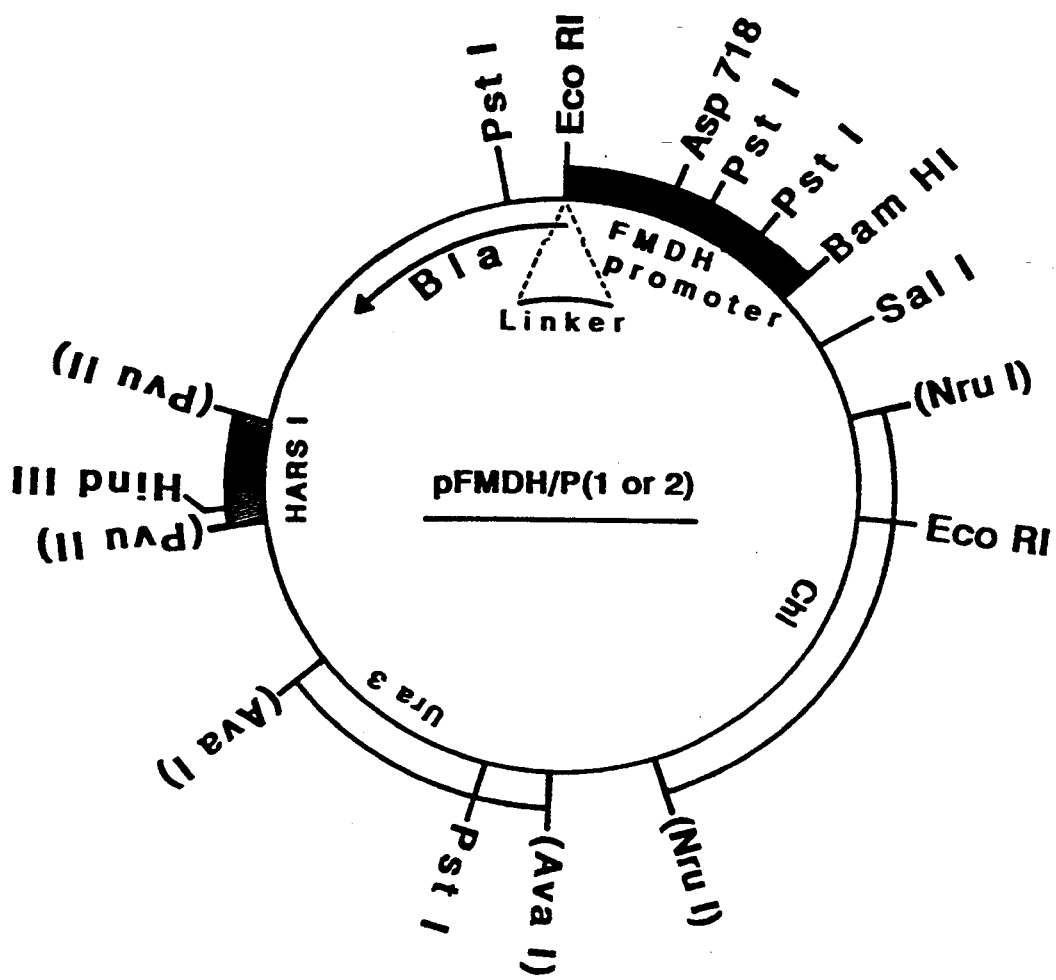

FIG. 6: Plasmid containing the fusion of bacterial β-lactamase gene with FMDH promoter.

Figure 7:
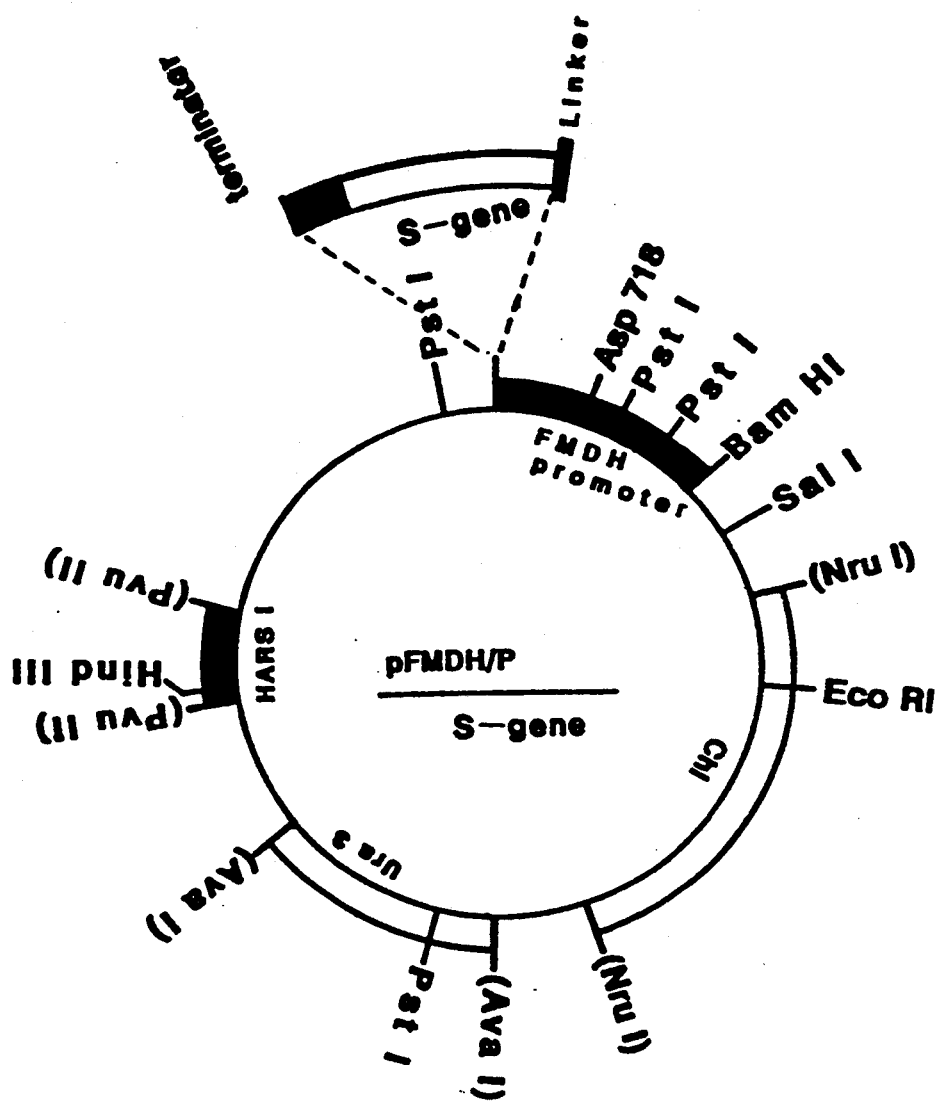

FIG. 7: Plasmid containing the hepatitis S-gene; HARS—H. polymorpha autonomous replicating sequence; URA3—S. cerevisiae gene; FMDH-promoter (−9 type promoter).

Figure 8:
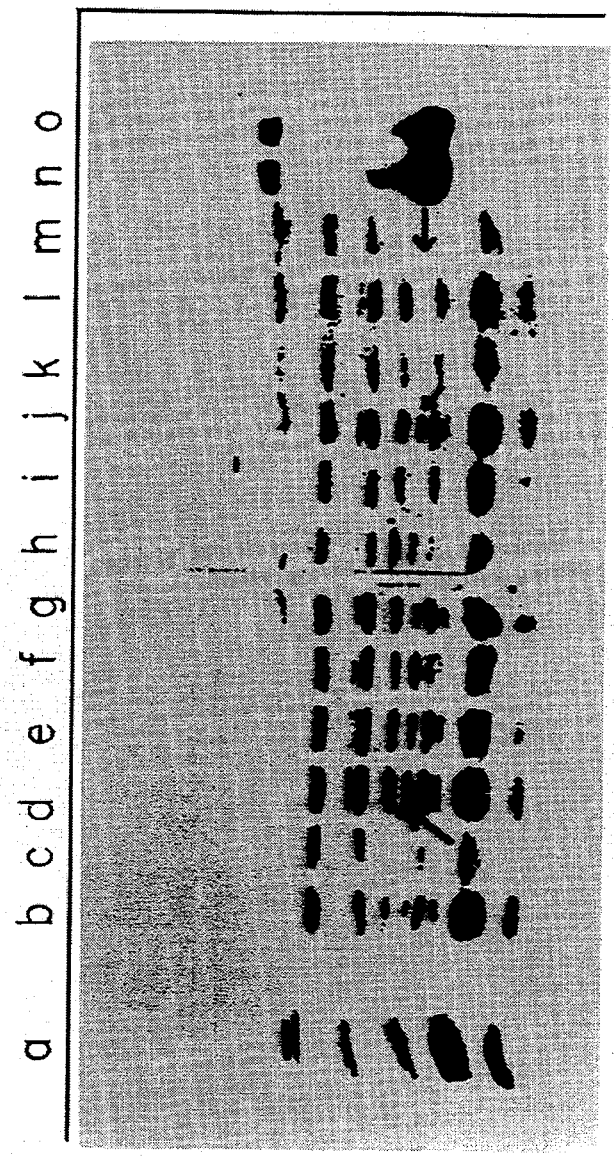

FIG. 8: Western blot-stained by peroxidase/protein A method. Polyclonal antibodies (not clarified) were used in this experiment:

Lane a: LR9 growth on methanol
Lane i: transformant w/o S-gene
Lanes k, l, m: transformants with S-gene grown on glucose (repression)
Lanes b, c, d, e, f, g: different transformants with S-gene grown on methanol
Lanes n, o: 500.450 ng purified HSBAg, respectively FIG. 9: Plasmid expressing α-amylase gene; symbols are the same as in FIG. 7.

Figure 10:
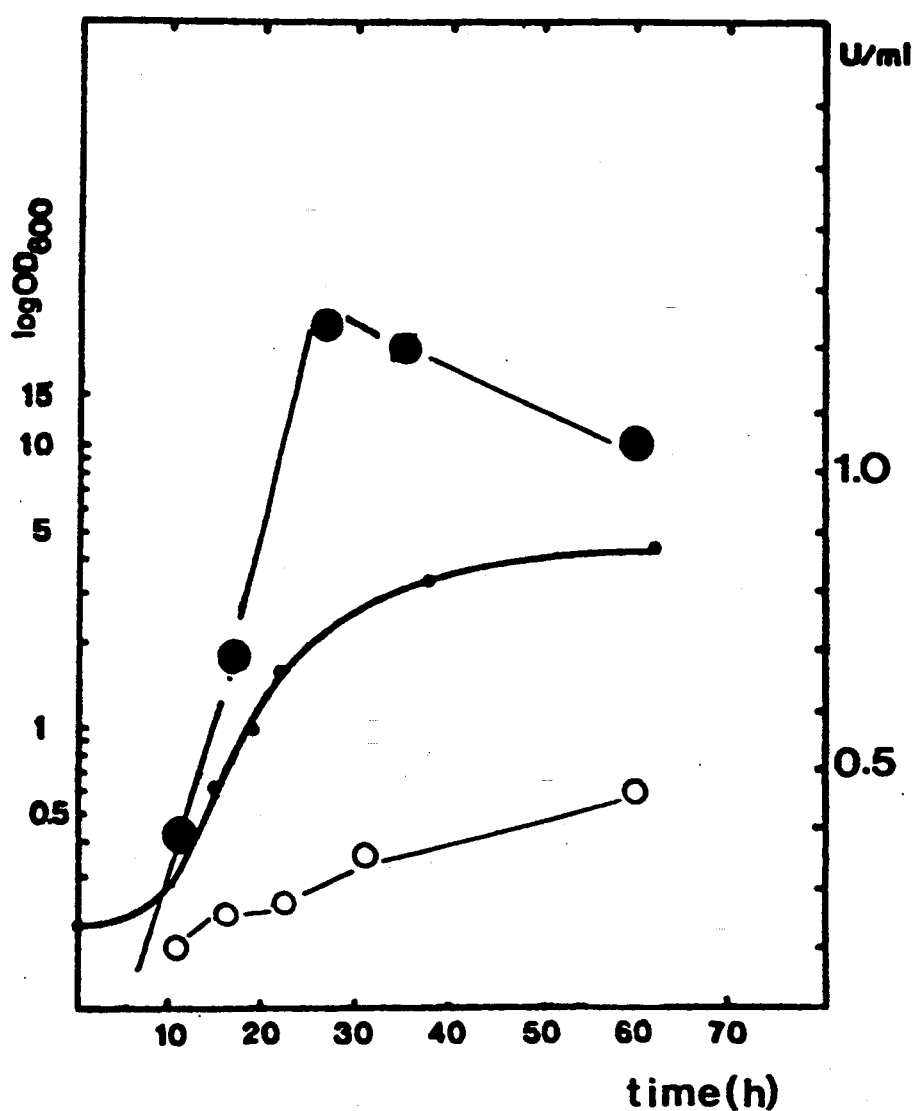

FIG. 10: Growth of transformants on medium containing methanol (induction). Enzyme activity (U/ml) were measured in medium and in cells (intra-cellular enzyme level). The latter value was expressed as corresponding to 1 ml of medium.

Figure 11:
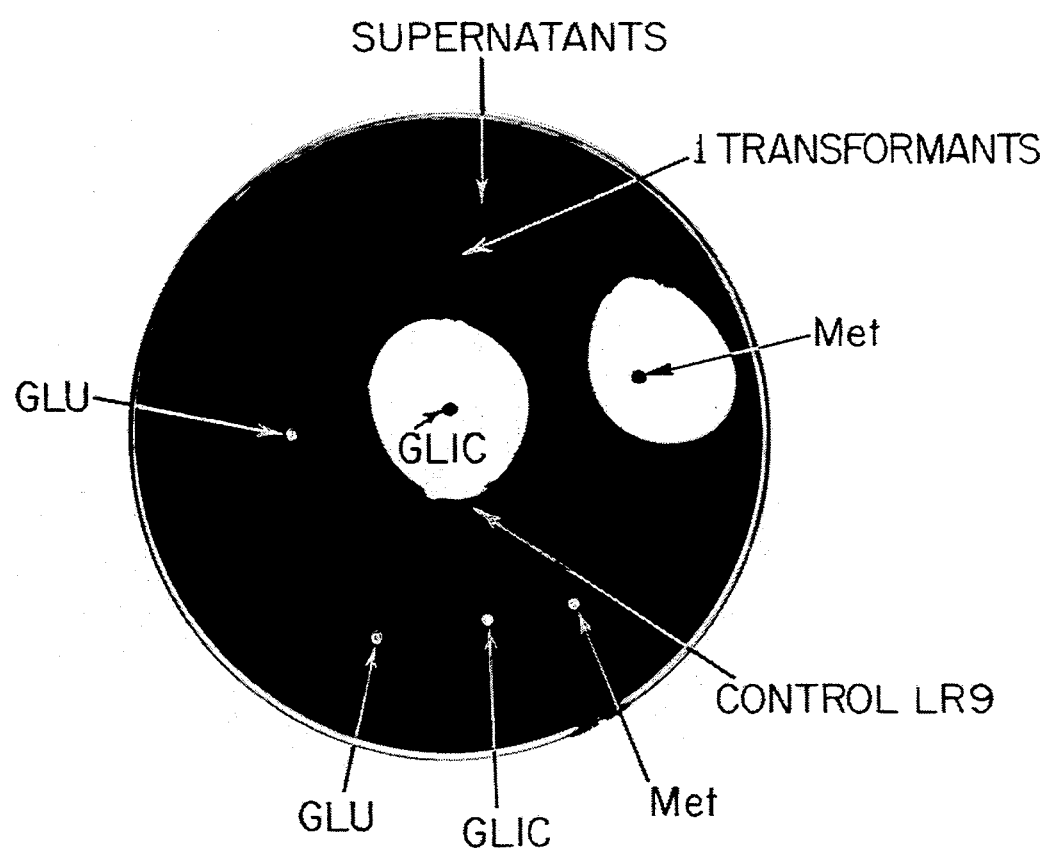

FIG. 11: The formation of halo after applying on the plate 50 ul of the medium from transformants (upper row) and from control untransformed strain LR9 (lower row).

Strains, media, vectors

Thermophilic, homothallic strain of H. polymorpha (ATCC 34438) was used. Yeast was grown at 37° C. on minimal YNB medium as described (3, 5). Induction of methanol utilisation system was achieved by growth in minimal medium containing 1% methanol; growth on 3% glucose minimal medium resulted in repression of the system.

E. coli L90; C600recA, hsdM, araB, was used for transformation;

E. coli JM103, thi, strA, supE, endA, sbcB, hsdR, F'traD36, proAB, lacI, ZM15, and
E. coli KH802 gal, met, supE, were used as host for phage M13 and for λ-vector Charon 4A, respectively. Plasmid DNA and RF M 13 were isolated by scaled-up alkaline minilysates methods (6) followed by CsCl ultracentrifugation, λ-vector Charon 4A and Charon 4 recombinant clones were isolated by scaled-up plate lysate methods (6).

H. polymorpha total DNA of the size greater than 50 kb was isolated from spheroplasts as previously described (5).

Charon 4 H. polymorpha DNA library was constructed by ligating partially EcoRI digested H. polymorpha DNA with Charon 4 arms as described previously (5).

PolyA mRNA from H. polymorpha and analysis of the mRNA by an in vitro cell free rabbit reticulocyte system is described previously (5).

mRNA labelling: mRNA was partially fragmented by mild alkaline treatment (7) and labelled at the 5'-end with $\gamma$-$^{32}$P-ATP (Amersham).

The differential plaque filter hybridisation was performed essentially as described in (12). Recombinant phages were plated to about 3,000 pfu per plate. Plaques from each plate were blotted into a set of 5-6 replica nitro-cellulose filters (BA85, Schleicher and Schüll). The filters were hybridized to appropriate $^{32}$P-mRNA or $^{32}$P-DNA probes in 5×SSPE. 50% formamide, containing additionally 150 ug/ml tRNA, 10 ug/ml poly A, 5×Denhardt's solution, 5 ug/ml rRNA from H. polymorpha isolated as described in (5, 6).

S1 mapping experiments were performed essentially as described by Favarolo et al. (8). S1 nuclease from NEN at concentration 1,000 units/ml was used.

Hybrid selection technique was performed as described by Büneman et al. (9). Briefly, DNA from recombinant subclones was covalently bound to DPTE derivative of Sephacryl S-500. Total mRNA was then hybridized with DNA/S-500 matrix. mRNA species not complementary to the immobilized DNA were washed out under very stringent conditions (5, 9). Hybridized mRNA was eluted with H$_2$O at 100° C. Hybrid selected mRNA was then translated in cell-free system, and the translation products analyzed by immunoprecipitation as described previously.

Sequence analysis: Different overlapping fragments derived from the exonuclease Bal31 digestion of DNA fragments encompassing FMDH gene were cloned into M13 phages mp9, mp8 and into plasmid pUC12, pUC13. The subcloned fragments were sequenced by Sanger et al. (10) and Maxam-Gilbert (11) methods.

Formate dehydrogenase was purified to homogeneity from methanol grown H. polymorpha cells as described elsewhere. Antibodies against FMDH, denaturated form, were raised in rabbits according to standard procedures.

Identification of mRNA species encoding FMDH

Figure 1:
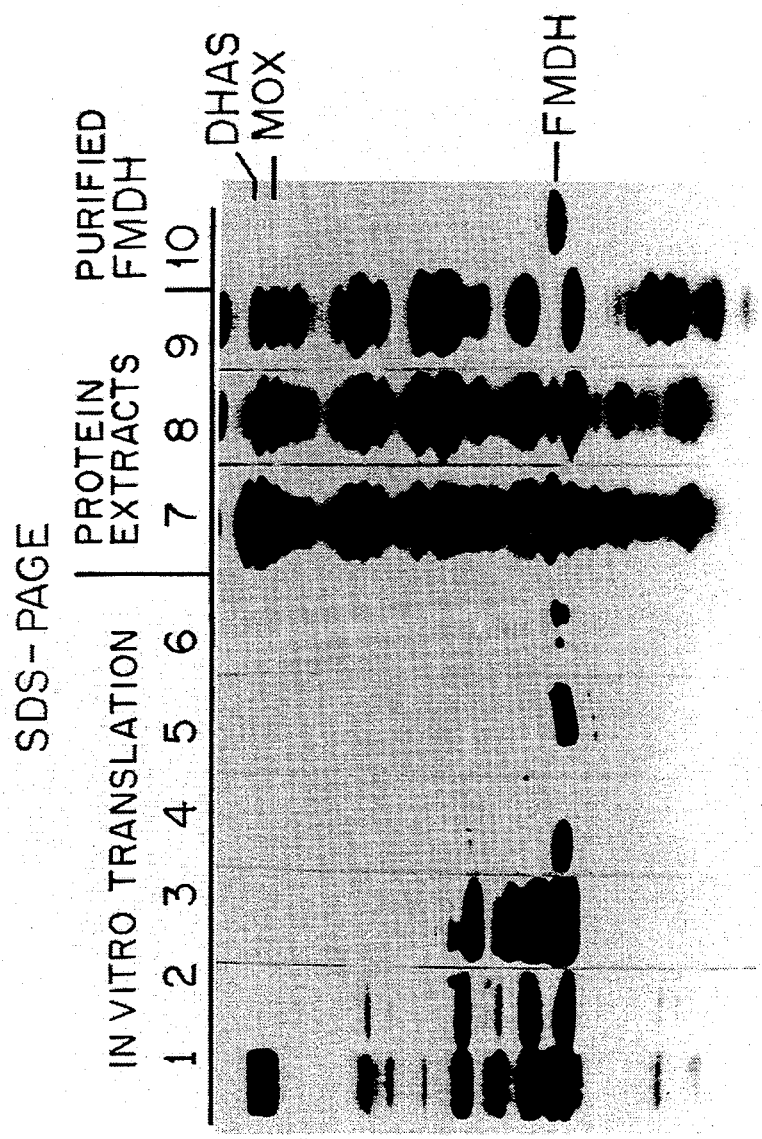
FIG. 1: Analysis of protein crude extracts and in vitro translation products by SDS-polyacrylamid gel electrophoresis.

In vitro translation products of total mRNA isolated from cells grown on 3% glucose (repression) or 1% methanol (induction) were analyzed on SDS-PAGE gels. FIG. 1 shows the comparison of in vitro translation products of mRNA from induced (lane 1), not induced (lane 2) cells, as well as the immunoprecipitates of the first preparation with specific antibodies directed against FMDH (lane 4). In addition, the electrophoretic patterns of crude protein extracts from 1% methanol, 0.5% glycerol/0.1% glucose (derepression) and 3% glucose cultures were compared with the electrophoretic mobility of purified FMDH (lanes 7, 8, 9 and 10 respectively).

The results obtained clearly identified the FMDH protein position on SDS-PAGE, and indicate that FMDH protein and its mRNA are predominant species in cells grown on methanol (induction). The position of two other predominant proteins, MOX and DHAS, is also indicated. FIG. 1 also points out that considerable expression is achieved under derepressed conditions (lane 8) and that 3% glucose represses the enzymes of methanol utilisation system. Above conclusions enabled us to isolate through sucrose gradient centrifugation mRNA fraction enriched in mRNA encoding FMDH (lane 3) in order to use it for screening procedure.

Screening for FMDH gene

The H. polymorpha DNA bank in Charon 4 phage was screened by differential plaque hybridisation (Materials and Methods) with radioactive $^{32}$P-labelled mRNA from induced, not induced cells and with $^{32}$P-mRNA from a fraction enriched in FMDH mRNA (FIG. 1, lane 3). Additionally, replica filters were hybridized with $^{32}$P-DNA probes from clones encoding MOX and DAS genes (3, 5). The latter was done to identify and eliminate the clones encoding the two other strongly inducible genes. Desired phages were selected and their DNA further characterized.

Characterisation of recombinant clones

The initial identification of a clone was achieved by hybrid selection technique, restriction mapping and establishing the size of the mRNA encoded by a given clone.

Hybrid selection

DNA from Charon4 recombinant clone JM was covalently bound to DPTE S-500 matrix, mRNA complementary to JM clone was selected and its in vitro translation products analyzed. FIG. 1 shows that the hybrid selected mRNA gives upon in vitro translation a major peptide product of the same elecrophoretic mobility as FMDH peptide (lane 5). When peptides from lane 5 were precipitated with specific antibodies (lane 6), a major band of a size of FMDH and additional weak band are visible. In control experiment with not-induced mRNA not detectable mRNA of FMDH character was selected by this technique. The presence of additional weak bands visible in lane 5 and 6 are probably artefacts of the used hybrid selection technique.

These data strongly suggest that clone JM contains FMDH gene.

Restriction map and the size and direction of transcription

Restriction map of clone JM and its subclones is shown in FIG. 2. DNA fragments encompassing the gene were identified by hybridizing the Southern blots with $^{32}$P-labelled induced mRNA.

8.5 kb EcoRI H. polymorpha DNA fragment from clone JM contains a gene. A further analysis allowed to subclone the gene and its presumptive regulatory regions on HindIII/EcoRI 4.1 kb fragments in pBR325.

S1 mapping

Non-radioactive HindIII/EcoRI 4.1 kb fragment from plasmid p3M1 was isolated and annealed with induced and not-induced mRNA. The size of DNA protected by its cognate mRNA against the action of nuclease S1 was analyzed by agarose electrophoresis followed by Southern blotting and hybridization with appropriate $^{32}$P-DNA in order to visualize the fragment. FIG. 3, lane 1 shows that induced mRNA protects 1.2 kb long DNA fragment. This indicates that the gene codes for a protein of about 35-37,000 daltons. This value was found for the FMDH protein. Since in this MW region FMDH is the only strongly inducible protein, this result supports the identification of the gene.

3' end of the gene, transcription direction and the amount of FMDH transcript

Two fragments containing the gene, 1.0 kb BamHI/PstI and 1.4 kg HindIII/BamHI, were isolated and a 3' end label was introduced at BamHI site. Only the label on the right (FIG. 3, lane 3-4), 1.4 kb HindIII/BamHI fragment was protected by annealing with mRNA indicating the direction of transcription from left to right (arrow in FIG. 2). This size of the band (lane 4) indicates that the 3' end of the gene is located 850 bp to the right of the BamHI site. This type of experiment was also used to roughly establish the amount of FMDH mRNA species in total polyA+ mRNA isolated from cells grown under different conditions. A known amount of $^{32}$P-3' end labelled DNA containing part of the gene was hybridized with varying amounts of mRNA. At DNA excess conditions, the radioactivity present in a band protected against S1 by a given amount of mRNA is a measure of the quantity of FMDH mRNA in the preparation. The data indicate that FMDH mRNA contributes about 7%±1% and 3% to 4% of total polyA+ mRNA in preparation from induced and derepressed growth condition respectively. FIG. 3, lanes a, b, c, d, shows the comparison of intensity of the DNA band resulting from S1 experiments where 3 ug of DNA was hybridized with 10 ug of total polyA+ mRNA. It is also clearly visible that in mid-log phase of 3% glucose (repression) cultures, only negligible amounts of FMDH transcript is visible whereas the same culture at stationary phase shows already considerable amounts of transcript. This is a good example of derepression phenomenon—in stationary phase, glucose is exhausted.

5' end of the gene 1.0 db BamHI/PstI fragment with a single 5' end label at BamHI yielded upon S1 mapping the multiple bands ranging from 255-265 bp (FIG. 3, lane 5). The comparison of this value with sequence data indicated that transcription starts around position −12 from the first ATG. The main band shows the start at "A" surrounded by pyrimidine track.

Nucleotide sequence

The nucleotide sequence of FMDH gene and encompassing region was determined by Sanger (10) and Maxam-Gilbert methods (11). The fragments to be sequenced were generated by deleting with Bal31 DNA containing the gene. FIG. 4 shows that all regions of the gene were sequenced several times in both directions. In case of doubts, M13 method data were corrected by data obtained by Maxam-Gilbert methods. The nucleotide sequence is presented in FIG. 5. The gene contains an open reading frame (ORF) of 1,020 nucleotides and code for a protein of 340 Da. The protein MW, calculated from these data, is 35,700 Da which agrees well with the values obtained by SDS-PAGE of purified protein. The gene was conclusively identified as FMDH by comparing the N-end of the gene as derived from DNA sequence with the data obtained by NH-end analysis of the purified protein.

5'-3' end regions

In the 5'-control regulatory region of eukaryotes, a consensus sequence −3A(9)XX1AUG4GX6py was reported to be required in efficiently transcribed and translated genes (12, 13). In FMDH gene, the rule is only partly followed where the sequence −3AUC+-1AUG+4AX+6A is present. The first ATG is proceeded by stop codons in all reading frames. The sequence CTATAAATA involved in eukaryotes in the initiation of transcription is found at position −40. Other features assumed to play a role in transcriptional control in yeast S. cerevisiae like CAACAA or CACACA (12) not present in FMDH.

In most of the yeasts studied until now, the gene 3' end region contains characteristic sequences which, according to some authors, play a role in proper termination of transcription and serve as polyadenylation signals (14, 15). Zared and Sherman (16), and Bennetzen and Hall (17) assumed that a sequence T-rich ... TAG ... TAGT(or TATGT) ... AT ... TTT or T ... TAAATAA ... A(or G) ... T ... A ... AT play these roles. In FMDH gene, similarity to these consensus sequences is rarely found. When looking for some potential signals, some repeating sequences were found. Sequences TTGGA and TAGG repeat twice. AAATATAA, similar to animal polyadenylation signal, is located 30 bp downstream from the end of ORF.

EXAMPLE 1

In order to be able to study the functional regions of FMDH 5' upstream region, a series of deletion of this region was isolated. First, to obtain the promoter without the structural gene, a pUC type plasmid containing the 1.4 kb Bam HI fragment was subjected to Bal31 exonuclease treatment after the plasmid was linearised at a proper point. At the beginning, attention was focused on the promoter fragment which had the deletion at the position −5 from the first ATG; the fragment is called "−5 promoter". Also "−9" deleted promoter was used in some experiments.

The "−5 promoter" was fused to the open reading frame of the bacterial β-lactamase gene (Bla). The gene was used in the laboratory as a very suitable model for studying the expression of foreign protein under the control of yeast promoters.

The signal sequence of the β-lactamase was not present in the construction obtained, thus enabling the measurement of enzyme activity in yeast protein extracts. The fused DNA fragment was cloned into the plasmid containing H. polymorpha autonomously replicating sequence (HARS1) (FIG. 6), and S. cerevisiae Ura3 gene which serves as a marker for H. polymorpha transformation. The amount of β-lactamase produced in H. polymorpha transformants was measured by the enzymatic and immuno-tests. Table 1 shows the synthesis of β-lactamase under the control of FMDH promoter in cells grown in different media (different carbon sources).

Table 1 shows that the isolated FMDH promoter is properly and stringently controlled by repression/-derepression/induction mechanism. The estimation of the amount of synthesized protein shows that the system of this invention is characterised by very efficient transcription and translation of the foreign protein. In the control experiment, β-lactamase was expressed in S. cerevisiae under the control of a strong S. cerevisiae PDC (puryvat decarboxykase) promoter on 2-um plasmid (50 copies per cell). The values obtained were lower than in the case of H. polymorpha by a factor of 5-6.

TABLE 1

| | Production of β-Lactamase | | | | | |
| | enzymatic test (U/mg protein) | | | immuno-test (% of total cell protein) | | |
| clone | GLU | GLIC | Met—OH | GLU | GLIC | Met—OH |
| --- | --- | --- | --- | --- | --- | --- |
| Lr 45 | 30 | 4,000 | 15,000 | — | 3–4 | 6–8 |
| L 5 | 70 | 10,000 | 28,000 | — | 6–8 | 10–12 |

GLU - grouwth on 3% glucose (repression)
GLIC - growth on 1% glicerol (depression)
Met—OH - growth on 1% methanol (induction)

In all cases, cells from late logarithmic phase were taken for measurement. The plasmid containing the fusion has 50-60 copies per cell.

EXAMPLE 2

Expression of genes encoding Hepatitis B surface antigens (HSBAg) under the control of FMDH promoter 1. Construction of the plasmid expressing the hepatitis proteins.

Hepatitis B 1,2 kb DNA fragment encodes a long S2-S1-S-protein (pre-s), which after processing (removal of S2-S1-part) is converted into the S-protein. Viral envelope consists of both proteins.

For our expression experiments we have used the 1,2 kb fragment as well as a shorter part of this DNA which encodes only S-protein. The latter is also able to form antigenic pseudo viral particles.

We have inserted both hepatitis S-gene into our universal vector. As shown in FIG. 1 and scheme 1 the vector contains autonomous replication sequence (HARS), URA3 gene from S. cerevisiae as a selective marker and H. polymorpha promoter followed by short linker. After the S-gene we have placed DNA fragment derived from H. polymorpha MOX gene exhibiting the transcription terminator function. FIG. 7 shows the construction containing the S-gene.

2. Transformation of H. polymorpha and screening for clones expressing HSBAg.

H. polymorpha URA3 mutant LR9 was transformed with the above described plasmids. The yeast transformants were then immediately screen for the expression of HBSAg using polyclonal antibodies. As an immunoscreening we have used Western blotting (peroxidase-protein A or to improve sensitivity $^{125}$J-protein A). The screening procedure was considerably impeded by the strong cross-reactivity of the sera with H. polymorpha crude extract proteins. We were, however, able to show the expressed antigen.

FIG. 8 shows the Western blotting Protein extracts from cells transformed with hepatitis gene grown on methanol and shows an additional antigenic band having the expected MW of S-protein. The control extracts from transformants grown on glucose (repression of FMDH promoter) do not have this band. The results shown in FIG. 8 are coming from transformants containing FMDH −9 promoter i.e. promoter derived by deleting the DNA fragment encompassing the promoter function till position −9 from the first ATG.

We analysed also by testing S1-nuclease mapping mRNA produced in our transformants. The results indicate that transformants are producing a lot of S-gene mRNA species and that the transcription is stringently controlled by repression/derepression/induction mechanism.

The above results were confirmed by positive RIA TEST of protein extracts derived from transformed cells. In the test the monoclonal antibodies directed against native S-protein were used.

EXAMPLE 3

Expression and secretion of α-amylase from Schwanniomyces castelli in H. polymorpha under the control of FMDH promoter.

To study the possibility of expressing in H. polymorpha a secretory protein we have chosen α-amylase gene from yeast S. castellii. The gene encodes the 56 kd protein which in S. castellii is totally secreted into the medium; this secretory process is accompanied by glycosilation of the protein.

Figure 9:
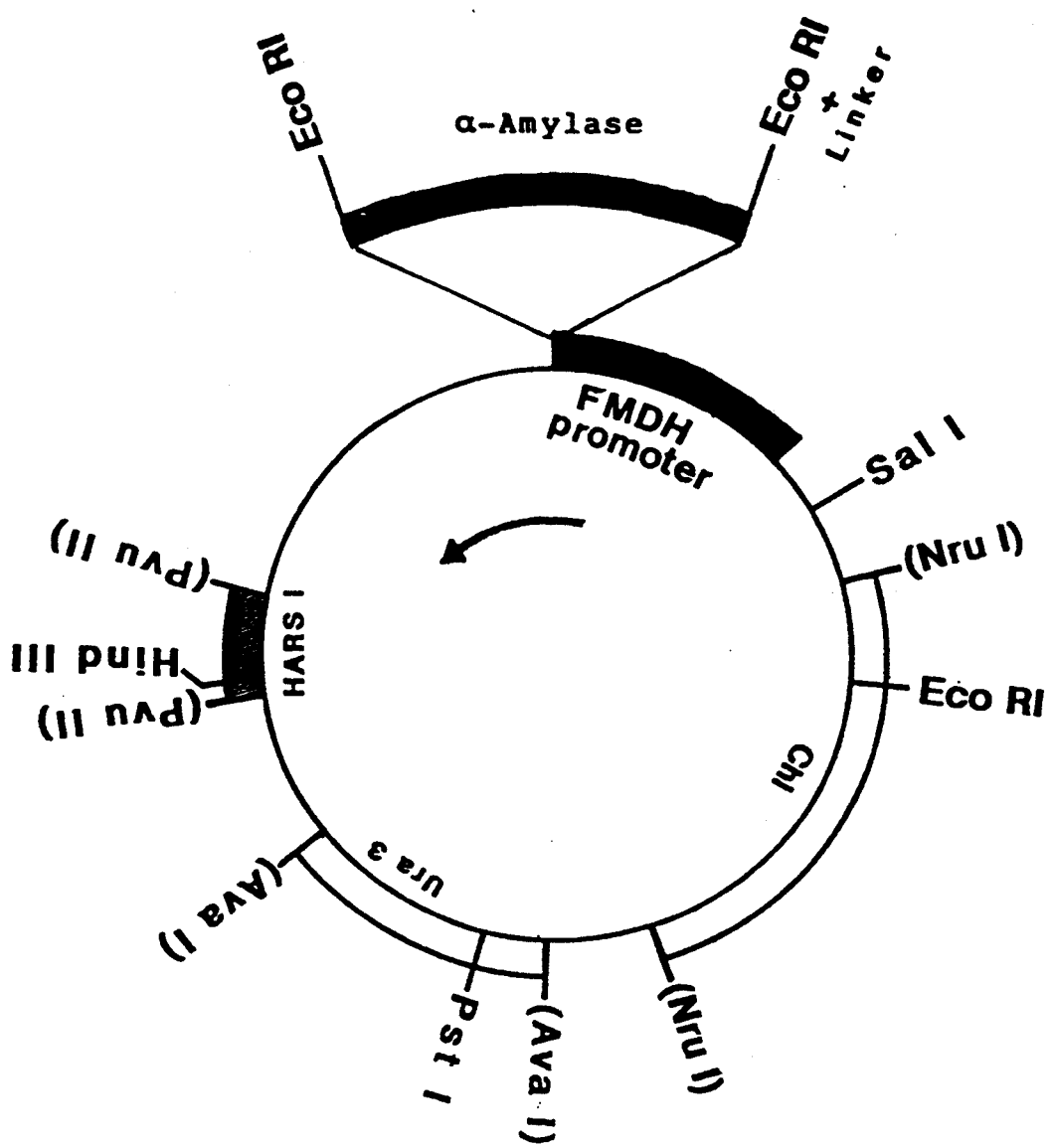

We have inserted EcoRI fragment encompassing the structural gene and its terminator into our expression plasmid (FIG. 9).

H. polymorpha was transformed with this plasmid and the transformants were tested for the expression and secretion of α-amylase using a starch degradation test (halo formation on starch-iodine plates) or enzyme kinetik test kit (α-amylase Merkotest A).

The results clearly show that α-amylase is produced under control of FMDH promoter. Moreover, the protein is secreted into the medium. FIG. 10 shows that in mid-log phase about 90% of the protein is secreted into the medium. Starch-iodine plate test confirmed these results (FIG. 11).

The data also show that it is possible to get a high expression level under derepressed conditions. This feature of the system is especially very valuable and important for biotechnological applications, i.e. the synthesis of foreign proteins can begin without addition of methanol as inducer simply by exhausting glucose in the medium and/or by the addition of glycerol. A system that can be handled in such an easy way by simultaneously providing a very effective expression yielding amounts of proteins applicable in the biotechnological industry has not been provided earlier.

In separate studies it has been shown that the other H. polymorpha promoters like MOX and DAS do not respond so strongly to derepression signals. In the case of DAS promoter, the expression under derepressed condition is additionally decreased by post-transcriptional control.

REFERENCES

1. Douma, A. L., Veenhuis, M., Koning, W., Evers, M., and Harder, W., Arch of Microbiol., (1985), 145, 237.
2. Roggenkamp, R., Janowicz, Z., Stanikowski, B. and Hollenberg, C. P. (1984) Mol. Gen. Genet. 194, 489-493.
3. Ledeboer, A. M., Maat, J., Visser, C., Bos, J. W. Verrips, C. T., Janowicz, Z., Eckart, M., Roggenkamp, R. and Hollenberg, C. P. (1985) Nucleic Acid Res., 3063.
4. Ellis, S. B., et al. Isolation of alcohol oxidase and two other methanol regulatory genes from the yeast Pichia pastoris. Molecular and Cellular Biology (1985) 5:1111-21.
5. Janowicz, Z. A., Eckart, M. R., Drewke, C., Roggenkamp, R. O., Hollenberg, C. P., Maat, J., Ledeboer, A. M., Visser, C. and Verrips, C. T., Nucl. Acid. Res. (1985) 13, 3043.
6. Williams, B. G. and Blattner, F. R. (1979) J. Virol. 29, 555.
7. Goldbach, R. W., Borst, P., Bollen-de-Boer, J. E. and van Bruggen, E. F. J. (1978) Biochem. et Biophys. Acta 521, 169-186.
8. Favarolo, J., Treisman, R. and Kamen, R. (1980) Methods in Enzymology 65, 718.
9. Bünemann, H., Westhoff, P. and Herrmann, R. G. (1982) Nucl. Acid. Res. 10, 7163-7178.
10. Sanger, F., Coulson, A. R., Barrell, B. G., Smith, A. J. H. and Roe, B. A. (1980) J. Mol. Biol. 143, 161-178.
11. Maxam, A. M. and Gilbert, Methods Enzymol. (1980) 65, 499.
12. van Dijken, S. P., Veenhuis, M. and Harder, W. (1982) Ann. N.Y. Acad. Sci. 386, 200-216.

13. Kozak, M. (1981) Nucl. Acid Res. 9, 5233–5252.
14. Sahm, H. (1977) Adv. Biochem. Eng. 6,77–103.
15. Veenhuis, M., van Dijken, J. P. and Harder, W. (1983) Adv. Microbiol. Physiol. 23,2–76.
16. Zaret, K. S. and Sherman, F. (1982) Cell 28, 563–573.
17. Bennetzen, J. H. and Hall, B. D. (1982) J. Biol. Chem. 257, 3018–3025.

We claim:

1. A process for producing a protein or polypeptide, comprising culturing a methylotrophic yeast containing a recombinant vector that contains an isolated DNA molecule comprising a 5' control region obtainable from a gene from a methylotrophic species of the genus Hansenula, said gene coding for a protein having formate dehydrogenase (FMDH) activity, derepressing said 5' control region by growth on glycerol as a carbon source, cultivating the methylotrophic yeast, and recovering the protein or polypeptide.

2. A process according to claim 1, further comprising inducing expression of the 5' control region by addition of methanol after the derepressing step.

3. An isolated DNA molecule comprising a 5' control region which is derepressed when grown on glycerol as the only carbon source and which is induced when methanol is added, said 5' control region obtainable from a gene from a methylotrophic species of the genus Hansenula, said gene coding for a protein having formate dehydrogenase (FMDH) activity.

4. An isolated DNA molecule according to claim 3, wherein the gene coding for the protein codes for a wild-type FMDH protein.

5. An isolated DNA molecule according to claim 3, which comprises the nucleotide sequences preceding the first ATG-codon of the structural gene as shown in FIG. 5(a).

6. An isolated DNA molecule according to any of claims 3 to 5, which DNA molecule is operably joined to a structural gene in order to bring said structural gene under the control of the 5'-control region of the FMDH gene.

7. An isolated DNA molecule according to claim 6, wherein the structural gene operably joined to the 5'-control region of the Hansenula FMDH gene encodes a methylotrophic yeast protein having formate dehydrogenase (FMDH) activity.

8. An isolated DNA molecule according to claim 6, which comprises the nucleotide sequence as shown in FIGS. 5a, b and c.

9. An isolated DNA molecule according to claim 6, wherein said structural gene encodes a foreign protein selected from the group consisting of
   (a) Hepatitis B Virus S1-S2-S protein,
   (b) Hepatitis B Virus S-antigen,
   (c) alpha-amylase from *Schwanniomyces castellii*,
   (d) glucoamylase from *Schwanniomyces castellii*, and
   (e) invertase from *Saccharomyces cerevisiae*.

10. An isolated DNA-molecule according to claim 3, wherein said isolated DNA-molecule has been obtained from one or a combination of genomic DNA or DNA of naturally occurring plasmids.

11. An isolated DNA molecule according to claim 3, wherein said DNA molecule is operably joined to DNA-sequences coding for secretory signals.

12. An isolated DNA molecule according to claim 11, wherein the secretory signals are selected from the group consisting of:
   *Hansenula polymorpha* membrane translocation signals,
   *Schwanniomyces castellii* amylase and glucoamylase signals,
   and *Saccharomyces cerevisiae* α factor and invertase signals.

13. An isolated DNA molecule according to claim 12, wherein the *Hansenula polymorpha* membrane translocation signal is selected from methanol oxidase and dihydroxyacetone synthase.

14. An isolated DNA molecule which comprises a DNA molecule obtainable from a gene from a methylotrophic species of Hansenula, said gene coding for a protein having formate dehydrogenase (FMDH) activity.

15. A recombinant vector, wherein said recombinant vector contains DNA-sequences according to claim 3.

16. A methylotrophic yeast which comprises a vector according to claim 15.

17. A methylotrophic yeast according to claim 16, which is a yeast of the genera Candida, Hansenula or Pichia.

18. A methylotrophic yeast according to claim 16, which has been transformed with an isolated DNA molecule according to claim 4.

19. A methylotrophic yeast according to claim 18, wherein the isolated DNA molecule has been integrated into the genome of the methylotrophic yeast or maintained as an extrachromosomal DNA molecule.

20. A methylotrophic yeast according to claim 16, which tolerates high concentrations of foreign proteins.

* * * * *